(12) United States Patent
Sandstrom

(10) Patent No.: US 11,007,277 B2
(45) Date of Patent: *May 18, 2021

(54) METHOD OF ATTACKING TARGET CELLS

(71) Applicant: Robert E. Sandstrom, Longview, WA (US)

(72) Inventor: Robert E. Sandstrom, Longview, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/991,352

(22) Filed: Aug. 12, 2020

(65) Prior Publication Data

US 2020/0368366 A1 Nov. 26, 2020

Related U.S. Application Data

(63) Continuation of application No. 15/576,558, filed as application No. PCT/US2016/047646 on Aug. 18, 2016, now Pat. No. 10,744,208.

(60) Provisional application No. 62/207,764, filed on Aug. 20, 2015.

(51) Int. Cl.
| | | |
|---|---|---|
| A61K 49/00 | (2006.01) | |
| A61K 39/00 | (2006.01) | |
| A61K 39/395 | (2006.01) | |
| A61K 47/69 | (2017.01) | |
| A61K 41/00 | (2020.01) | |
| A61K 47/68 | (2017.01) | |
| A61P 35/00 | (2006.01) | |
| A61K 9/00 | (2006.01) | |
| A61N 1/40 | (2006.01) | |

(52) U.S. Cl.
CPC ........ *A61K 47/6929* (2017.08); *A61K 9/0009* (2013.01); *A61K 39/395* (2013.01); *A61K 41/0028* (2013.01); *A61K 41/0052* (2013.01); *A61K 47/68* (2017.08); *A61K 47/6849* (2017.08); *A61N 1/406* (2013.01); *A61P 35/00* (2018.01); *A61K 2039/60* (2013.01); *A61K 2300/00* (2013.01)

(58) Field of Classification Search
CPC .............................. A61K 49/00; A61K 39/395
USPC .................. 424/9.1, 9.2, 130.1, 138.1, 178.1
See application file for complete search history.

(56) References Cited

U.S. PATENT DOCUMENTS 10,744,208 B2 * 8/2020 Sandstrom ............. A61K 47/68

* cited by examiner

*Primary Examiner* — Rodney P Swartz
(74) *Attorney, Agent, or Firm* — Timothy E. Siegel Patent Law, PLLC; Timothy E. Siegel

(57) ABSTRACT

A method of killing cells of a targeted cell type in a patient body that utilizes nanoparticles having a first portion, which when exposed to a target portion of a targeted cell type, binds to the target portion and a second portion, joined to the first portion, and comprised of a low resistivity material. The nanoparticles are introduced into a contact area where they contact cells of the targeted cell type. Contemporaneously, the contact area is exposed to a varying magnetic field of insufficient strength to increase the temperature of any part of the patient body by more than ten degrees Celsius, but which creates a current at the nanoparticles sufficient to disrupt function of the targeted cell type.

22 Claims, 3 Drawing Sheets

METHOD OF ATTACKING TARGET CELLS

RELATED APPLICATIONS

This application is a continuation of application U.S. Ser. No. 15/576,558 filed on Nov. 22, 2017, now U.S. Pat. No. 10,744,208, issuing Aug. 18, 2020, which itself claims benefit of PCT application No. PCT/US2016/047646, filed on Aug. 18, 2020, which itself claims benefit of application U.S. Ser. No. 62/207,764 filed on Aug. 20, 2015, all of which are incorporated by reference as if fully set forth herein.

TECHNICAL FIELD

The field of the invention is the field of medical use of nanoparticles to attack target cells by creating an electrical current through magnetic induction.

BACKGROUND

An electric current of sufficient strength applied to a cell will kill the cell. Multiple patterns of cell damage may contribute to the death of the cell. Cells maintain their physiologic integrity by maintaining charge separation across the cell membrane and by maintaining intracellular compartments with separating membranes (e.g. mitochondria). An electric current of sufficient strength disrupts cell membranes by a process termed "irreversible electroporation." In addition, an electric current of sufficient strength can affect cells through mitotic disruption, thermal effects, and induction of apoptosis. Electric currents have been applied to cells by invasive methods including the application of electrodes. Methods have been proposed to ablate tumor cells by the application of low frequency and/or radiofrequency radiation and modifying pulse frequency, pulse duration, electric current, magnetic flux density and treatment duration with the object of altering genetic regulation. Another proposed method employs polymer-coated gold nanoparticles and an external magnetic field to induce eddy currents and thermal damage in tumor cells. Unfortunately, none of the above described methods have fully addressed the problem of cancerous or pathogenic cells in a human or animal body, and these cells continue to cause serious problems to patients.

SUMMARY

The following embodiments and aspects thereof are described and illustrated in conjunction with systems, tools and methods which are meant to be exemplary and illustrative, not limiting in scope. In various embodiments, one or more of the above described problems have been reduced or eliminated, while other embodiments are directed to other improvements.

In a first separate aspect the present invention may take the form of a method of killing cells of a targeted cell type in a patient body or blood, that utilizes nanoparticles having a first portion, which when exposed to a target portion of a targeted cell type, binds with specificity to the target portion and a second portion, joined to the first portion, and comprised of a low resistivity material. The nanoparticles are introduced into the patient body where they contact and bind cells of the targeted cell type. Subsequently, the patient body or blood is exposed to a varying electromagnetic field of insufficient strength to increase the temperature of any part of the patient body by more than ten degrees Celsius, but which creates a current at the nanoparticles sufficient to disrupt the function of the targeted cell, typically leading to cell death.

In a second separate aspect, the present invention may take the form of a nanoparticle, comprising a first portion, which when exposed to a target portion of a targeted cell type, binds with specificity to the target portion and a second portion, joined to the first portion, and comprised of a low resistivity material.

In a third separate aspect, the present invention may take the form of a liquid suspension, for administering to a patient, comprising nanoparticles, each comprising a first portion, which when exposed to a target portion of a targeted cell type, binds with specificity to the target portion; and a second portion, joined to the first portion, and comprised of a low resistivity material, the particles being suspended in a biocompatible liquid.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

PREFERRED MODES OF PRACTICING THE INVENTION

Definition

Figure 1:
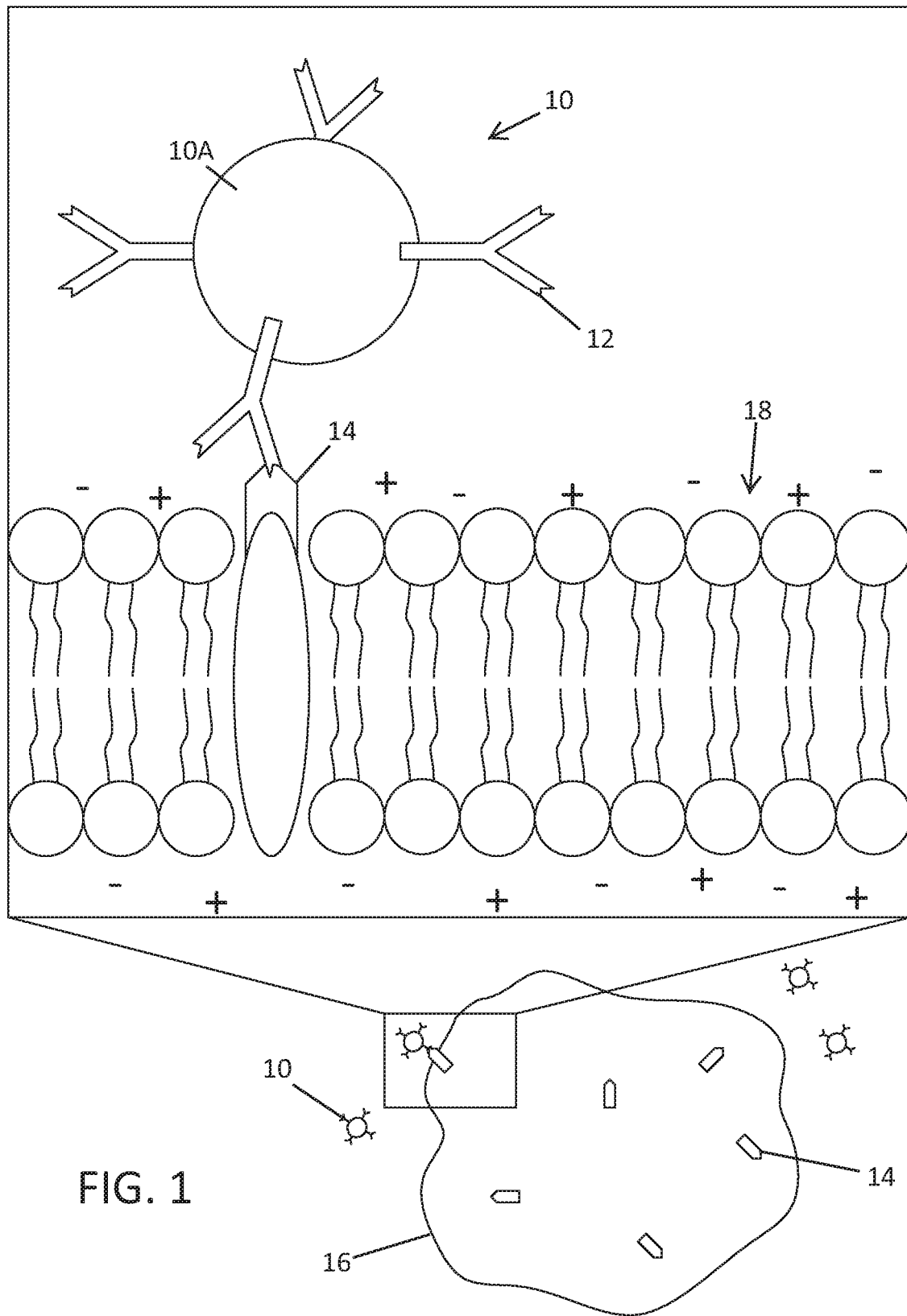
FIG. 1 is an illustration of a nanoparticle attaching to an antigen on a cell wall.

A low resistivity material is a material which at 20° C. has a resistivity of less than 6×10-4 Ohm·Meters.

Advances in material sciences and biology have resulted in the development of nanomaterials to include quantum wells, quantum wires (e.g. nanotubes and nanowires), and quantum dots which can be formulated to incorporate conductive metals such as gold, copper and silver. These nanomaterials can be functionalized by the incorporation of targeting antibodies, aptamers, and synthetic ligands. Such targeted nanomaterials can be structured as a nanoplatform which incorporates additional components to include recognition elements e.g.

folic acid or therapeutic modalities to include chemotherapeutic drugs. Among a wide range of antibodies that target tumor cells and have been incorporated into nanostructures, antibodies directed at CD20, CEA, and PSA have been demonstrated to selectively attach to tumor cells. Additionally, neoantigens specific for a specific tumor can be generated in the course of tumor genesis and can provide targeting options for synthetic ligands, antibodies, or aptamers, which are single stranded oligonucleotides which can be synthesized and selected for their binding specificity to targets such as proteins (e.g., interleukin-11 receptor alpha), lipids and cell membrane components, intracellular antigens presented by major histocompatibility complexes, or cell structural elements. Nanostructures incorporating a specific low resistivity metal and incorporating a targeting ligand will selectively attach to a cell component often in a predictable architectural pattern e.g., attached to the surface cell membrane or penetrating the cell membrane. Nanomaterials including conductive metal nanomaterials may also be incorporated into protocells which are cell-like nanocarriers composed of mesoporous silica nanoparticles enveloped with a lipid bilayer. Protocells can be loaded with drug or metal cargoes and can be targeted by ligands to include 30 antibodies, aptamers, and synthetic peptides. Protocells can selectively attach to a targeted cell and transload to the target cell a metallic conductor in the process of membrane fusion with the target cell.

As defined by Faraday's Law, an electromotive force (emf) is induced in a conductor when the magnetic field surrounding it changes. The magnitude of the emf is proportional to the rate of change of the magnetic field, given by the following equation:

$$\varepsilon = \frac{d\phi_B}{dt}$$

where E is the emf and $\phi_B$ is the magnetic flux. Upon exposure to a magnetic field, metal nanoparticles at the cell surface will experience an emf measured as an electrical current. That current will be determined by the electrical conductivity of the metal, its concentration, its membrane deposition or incorporation and by the magnetic flux. Magnetic flux will be determined by the magnetic field strength and movement of the target or the magnet field. The magnetic field may be generated by a ferromagnetic magnet to include iron, nickel, cobalt and rare earth metals and alloys or by an electromagnet. The flux strength will be determined by the inherent strength of the source magnet, the distance from the source magnet, and the magnetic susceptibility of any interposed material. A magnetic field can be contoured to achieve selective current flow based on positioning, shielding, and contouring of the field by the employment of magnetic arrays which can provide a magnetic field of variable strength across an anatomic field.

Magnetic flux can also be created by an electromagnet with an alternating electrical field. The frequency of the electromagnetic field will directly relate to the magnetic flux strength. Positioning, magnetic insulators and shielding can be employed to contour and focus the magnetic flux field created.

Externally positioned magnets can be structured to provide a rotational field in multiple dimensions or planes to accommodate selective injury currents in tissues susceptible to magnetic induction with the strength of the current dictated by the choice of metal employed and the concentration of the nanostructures and by the selectivity and concentration of the ligand e.g. tissue specific antibody. Higher conductive metals such as gold, silver and copper offer distinct advantages over alternatives like iron. The conductivities of gold, silver and copper are an order of magnitude higher than iron. Gold, silver and copper will bind at significantly lower concentrations in normal cells and hence bystander effects are less likely to be encountered. Gold, silver and copper have less inherent cell toxicity for normal cells and secondary injury is less likely than for many alternative metals. The proposed method, in addition, benefits from selective targeting of a cell population exposed to a focused magnetic flux field.

Cell viability is in large part determined by the ability of the cell, through a complex set of structures, to maintain charge separation across the cell membrane wall. Similar considerations apply to intracellular structures which may be targeted by metal ligands. Ligand attachment to specific intracellular targets such as the nuclear membrane, ribosomes, mitochondria, or chromosome sites, or to nucleic acid moieties, can additionally attach metal nanomaterials selectively and permit current induction as described at the target site.

Charge separation across the cell membrane can be disrupted by irreversible electroporation which can be induced by low intensity fields of the order of magnitude of 100 V/cm for durations of 24 milliseconds. Such electrical field intensities and duration are achievable with membrane surface deposition of metallic nanostructures at concentrations of ten to five hundred ligands per cell. The density of ligands present in each cell, as well as changes in variables such as ligand affinity and the use of more complex targeting structures such as nanocells, may alter the load requirements.

Irreversible electroporation results in cell death. Alternative effects related to an induced current can result in targeted cell death by other means such as thermal effects, mitotic disruption, apoptosis, necrosis and direct damage to mitochondria, ribosomes and nuclear membranes, chromosomes and DNA.

Figure 2:
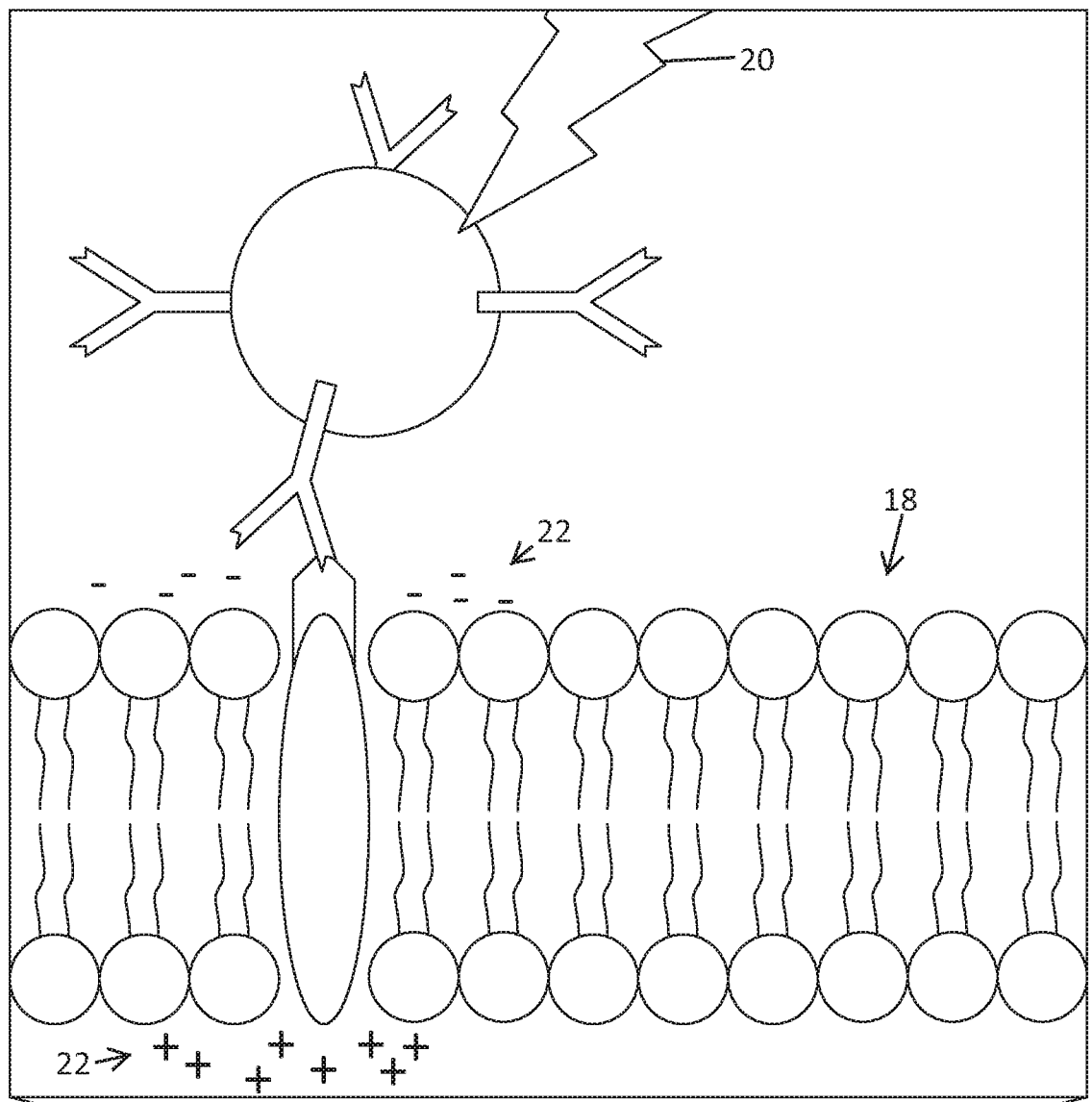
FIG. 2 is an illustration of the arrangement of FIG. 1, and wherein a magnetic field is applied to the nanoparticle and induces a current.
Figure 2:
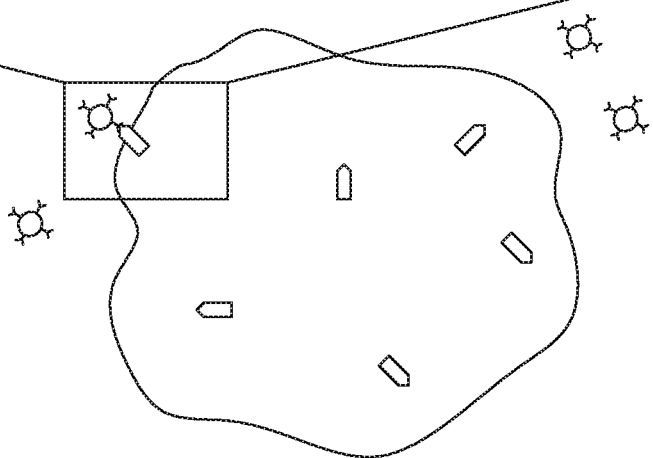
Figure 3:
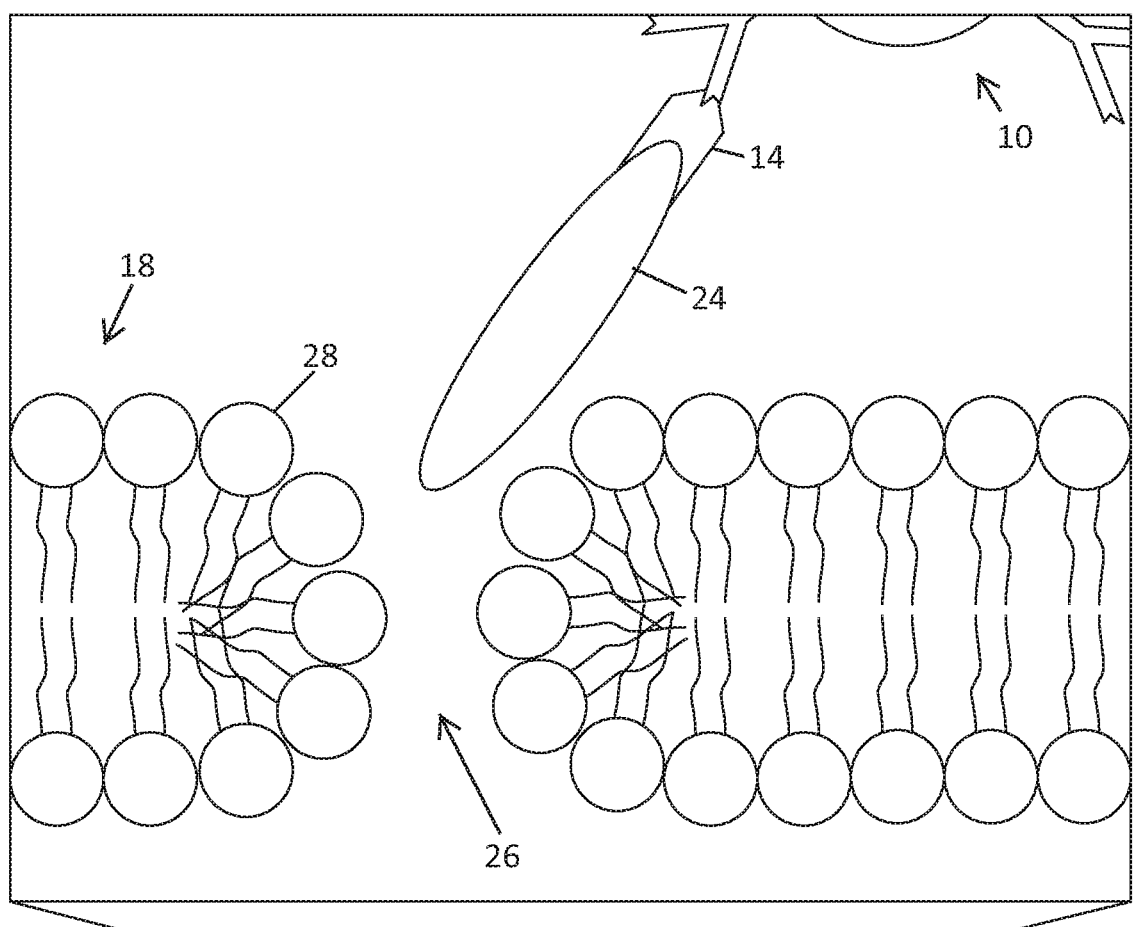
FIG. 3 is an illustration of a situation progressing from the arrangement of FIG. 2, wherein the nanoparticle has caused irreversible cell poration.
Figure 3:
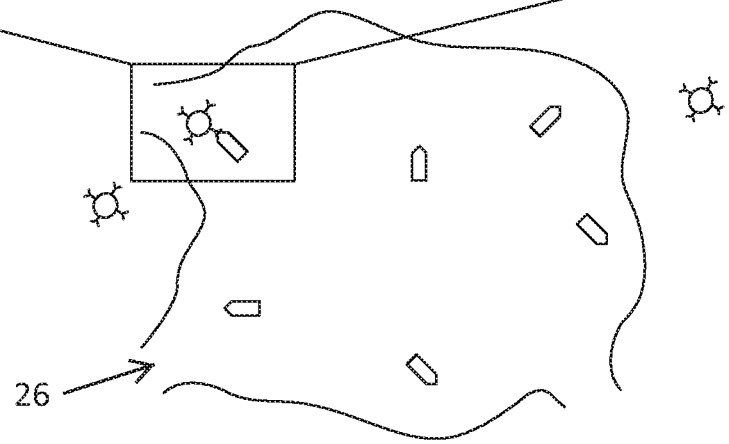

In one preferred embodiment, a patient is administered a concentration of copper nanowires 10A as a component of a nanostructure 10 which includes an antibody 12 with specificity for a specific antigen 14. Tumor cells 16 display these antigens 14 on the outer surface of the cell membrane 18, thus attracting and binding antibody receptors 12 attached to the nanostructures 10 (FIG. 1). The patient is then positioned in a device resembling a Magnetic Resonance Imaging scanner. The device applies a focused magnetic field selectively as determined by the anatomic parameters specific to the patient and tumor. Shielding and magnetic insulation can be employed to further contour the magnetic flux. A focused rotational magnetic field is created in the device such that the patient is exposed to a magnetic flux of sufficient strength to induce a current 20. Now bound at multiple points along the tumor cell membrane 18, the copper nanowires component 10A of the nanostructures 10 may conduct induced current 20, disrupting the charge distribution 22 along the cell membrane in the immediate area, as shown in FIG. 2. Antigens 14 may be displayed by integral membrane proteins, lipids and cell membrane components, major histocompatibility complexes, or cell structural elements 24. In irreversible electroporation, disrupting the charge distribution creates perforations 26 in the cell membrane as the polar phospholipids 28 reorient, as shown in FIG. 3. The length of exposure and magnetic field strength will be determined by patient specific, tumor specific, and anatomic parameters. The magnetic field may be conformed in multiple planes to assure maximum focused effect.

The above described method of treatment may be performed multiple times in sequence, to have an enhanced effect. In a preferred embodiment, daily treatments are given. In other preferred embodiments, a treatment is given every two days, or every three days or every four days, or every five days or every six days, or once a week.

In an embodiment, the techniques described above may be combined with chemotherapy, radiation therapy or immunotherapy. Accordingly, tumor or cancerous cells that have their cell membranes damaged may be killed by either the chemotherapy agent or free radicals that are then able to enter the cell or their intracellular components might be processed by immune cells, to activate biological processes leading to immune-mediated cancer cell death. For example, in an embodiment, Adriamycin is administered at the same time as the above recited techniques are used. In another example, gamma ray radiation, aimed at a tumor location is used contemporaneously with the method described above, thereby creating free radicals that can invade tumorous cells that have been opened by electroporation.

In one example of the preferred embodiment, a patient with a lung tumor that binds with a high degree of specificity to a subset of EGFR antibodies is treated with an intravenous preparation of the said antibody 12 which is a component of a nanoparticle 10 which includes a copper nanowire 10A such that from 100 to 500 nanoparticles attach to each tumor cell 16. The patient is then treated in a cylindrical electromagnetic pulse generator resembling an MRI device which focuses an alternating current magnetic field contoured to the tumor site with shielding to limit the anatomic field treated. The tumor is treated with a 1 Tesla magnetic field at 0.6 MHz frequency. The targeted tumor cells 16 are exposed to a 0.5 V transmembrane potential of sufficient strength to cause tumor cell 16 death through metabolic disruption to include irreversible electroporation.

In another example of the preferred embodiment, a patient with a hematologic malignancy, such as lymphocytic leukemia, is administered a preparation of an antibody 12, which is a component of nanoparticle 10, that binds with a high degree of specificity to antigenic sites 14 of the cancerous lymphocytes or leukemia cells (also represented by tumor cell 16). Nanoparticle 10 includes the antibody 12 and a copper nanowire 10A such that from 100 to 500 nanoparticles attach to each leukemia cell 16 in the patient's blood. The patient is then treated with a magnetic generator which is comparable to a dialysis machine in that the patient's blood is treated extracorporeally, such that the patient's blood is pumped into the device and exposed to an alternating current magnetic field. The blood is treated with a 1 Tesla magnetic field at 0.6 MHz frequency, thus exposing nanoparticle-bound lymphocytes to a 0.5 V transmembrane potential of sufficient strength to cause leukemia cell death through metabolic disruption to include irreversible electroporation. The treated blood is then returned to the patient.

INDUSTRIAL APPLICABILITY

The present invention finds industrial applicability in the production and use of nanoparticles and in the production and use of designed magnetic field generation devices. While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A method of killing cells of a targeted cell type in a patient, comprising:
   (a) providing nanoparticles having:
      (i) a first portion, of a type taken from a group consisting of: an antibody and an aptamer, which when exposed to a target portion of a targeted cell type, binds with specificity to said target portion; and
      (ii) a second portion, joined to said first portion, and comprised of a low resistivity material;
   (b) introducing said nanoparticles into a contact area where they can contact said cells of said targeted cell type;
   (c) exposing said contact area to a varying magnetic field of insufficient strength to damage said patient, but which creates a current at said nanoparticles sufficient to disrupt functioning of said targeted cell type.

2. The method of claim 1, wherein said contact area is within the patient's body.

3. The method of claim 1, wherein said contact area is an extracorporeal container, having said patient's blood passing therethrough.

4. The method of claim 1, wherein said first portion includes an antibody that when exposed to a target portion of a targeted cell type, binds with specificity to said target portion.

5. The method of claim 1, wherein said first portion includes an aptamer that when exposed to a target portion of a targeted cell type, binds with specificity to said target portion.

6. The method of claim 5, wherein said aptamer is a nucleic acid aptamer.

7. The method of claim 5, wherein said aptamer is a peptide aptamer.

8. The method of claim 1, wherein said low resistivity material is selected from a group consisting of gold, silver, copper, aluminum, and an alloy containing one or more of gold, silver, copper, and aluminum.

9. The method of claim 1, wherein said target portion is a portion of the outer cell membrane.

10. The method of claim 9, wherein irreversible electroporation is caused.

11. The method of claim 1, wherein said method results in an interruption of normal physiologic processes governed by electrical properties of each said cell of said targeted type, resulting in cell death.

12. The method of claim 1, wherein said target portion is taken from a group consisting of a cellular protein, a peptide, a lipid, and other targetable antigenic cell component.

13. The method of claim 1, wherein said method causes the interruption of normal physiologic processes governed by electrical properties of each said cell of said targeted type.

14. The method of claim 1, further accompanied by concurrent chemotherapy.

15. The method of claim 1, further accompanied by concurrent radiation therapy.

16. The method of claim 1, further accompanied by concurrent immuno therapy.

17. The method of claim 1, further being repeated periodically.

18. The method of claim 1, further wherein said varying magnetic field has a frequency of about 0.6 MHz.

19. The method of claim 1, further wherein said varying magnetic field has a frequency of greater than 0.1 MHz.

20. The method of claim 2, wherein said magnetic field is produced by an electromagnet outside of said patient's body.

21. The method of claim 1, wherein said magnetic field has the strength of about 1 Tesla at said contact area.

22. The method of claim 1, wherein said magnetic field exposes targeted cell types at said contact area to 0.5 V transmembrane potential.

* * * * *